US012588882B2

(12) United States Patent
Fujimoto et al.

(10) Patent No.: US 12,588,882 B2
(45) Date of Patent: Mar. 31, 2026

(54) ENERGY SUBTRACTION PROCESSING APPARATUS, ENERGY SUBTRACTION PROCESSING METHOD, RADIATION IMAGING SYSTEM, AND NON-TRANSITORY COMPUTER-READABLE STORAGE MEDIUM

(71) Applicant: CANON KABUSHIKI KAISHA, Tokyo (JP)

(72) Inventors: Ryuichi Fujimoto, Tokyo (JP); Atsushi Iwashita, Tokyo (JP); Kosuke Terui, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 321 days.

(21) Appl. No.: 18/302,018

(22) Filed: Apr. 18, 2023

(65) Prior Publication Data

US 2023/0404505 A1    Dec. 21, 2023

(30) Foreign Application Priority Data

May 23, 2022    (JP) ................................. 2022-083993

(51) Int. Cl.
*A61B 6/00*        (2024.01)
*G06T 7/00*        (2017.01)
*G16H 50/20*        (2018.01)

(52) U.S. Cl.
CPC ............ *A61B 6/482* (2013.01); *G06T 7/0012* (2013.01); *G16H 50/20* (2018.01); *G06T 2207/10116* (2013.01); *G06T 2207/30008* (2013.01)

(58) Field of Classification Search
CPC ..... A61B 6/482; A61B 6/4216; A61B 6/4233; A61B 6/487; A61B 6/5258; A61B 6/585;
(Continued)

(56) References Cited

U.S. PATENT DOCUMENTS 5,850,465 A * 12/1998 Shimura ................ G06V 10/44
                                                        128/920
9,035,265 B2    5/2015 Yagi
(Continued)

FOREIGN PATENT DOCUMENTS

CN        1324498 A    * 11/2001    ........... H10H 20/819
JP     2019162358 A    * 9/2019    ............ H04N 23/30
JP     2020203083 A    * 12/2020

OTHER PUBLICATIONS

Harrington, Donald P., Lawrence M. Boxt, and Philip D. Murray. "Digital subtraction angiography: overview of technical principles." American Journal of roentgenology 139.4 (1982): 781-786. (Year: 1982).*

*Primary Examiner* — Edwin C Gunberg
*Assistant Examiner* — Richard O Toohey
(74) *Attorney, Agent, or Firm* — Carter, DeLuca & Farrell LLP

(57) ABSTRACT

An information processing apparatus obtains a plurality of results by performing energy subtraction processing for each of a plurality of sets which are sets each formed from a plurality of radiation images corresponding to different radiation energies and in which combinations of radiation energies are different, and determines a value of a predetermined parameter used in the energy subtraction processing such that a dispersion between the plurality of results is reduced.

17 Claims, 9 Drawing Sheets

(58) Field of Classification Search
    CPC ..... A61B 6/505; A61B 6/5205; A61B 6/5217;
        G06T 7/0012; G06T 2207/10116; G06T
        2207/30008; G16H 50/20; G16H 30/20;
        G01T 1/1663; G01T 1/362; G01T 1/366
    See application file for complete search history.

(56)                    References Cited

U.S. PATENT DOCUMENTS

| | | | |
|---|---|---|---|
| 9,239,390 | B2 | 1/2016 | Sato |
| 9,360,562 | B2 | 6/2016 | Sato |
| 9,417,333 | B2 | 8/2016 | Sato |
| 9,910,169 | B2 | 3/2018 | Iwashita |
| 10,234,574 | B2 | 3/2019 | Iwashita |
| 11,422,098 | B2 | 8/2022 | Iwashita |
| 2014/0320685 | A1 | 10/2014 | Takenaka |
| 2020/0408933 | A1 | 12/2020 | Iwashita |
| 2022/0365004 | A1 | 11/2022 | Iwashita |
| 2023/0153970 | A1 | 5/2023 | Iwashita |
| 2023/0263492 | A1 | 8/2023 | Yamazoe |

* cited by examiner

F I G.  2
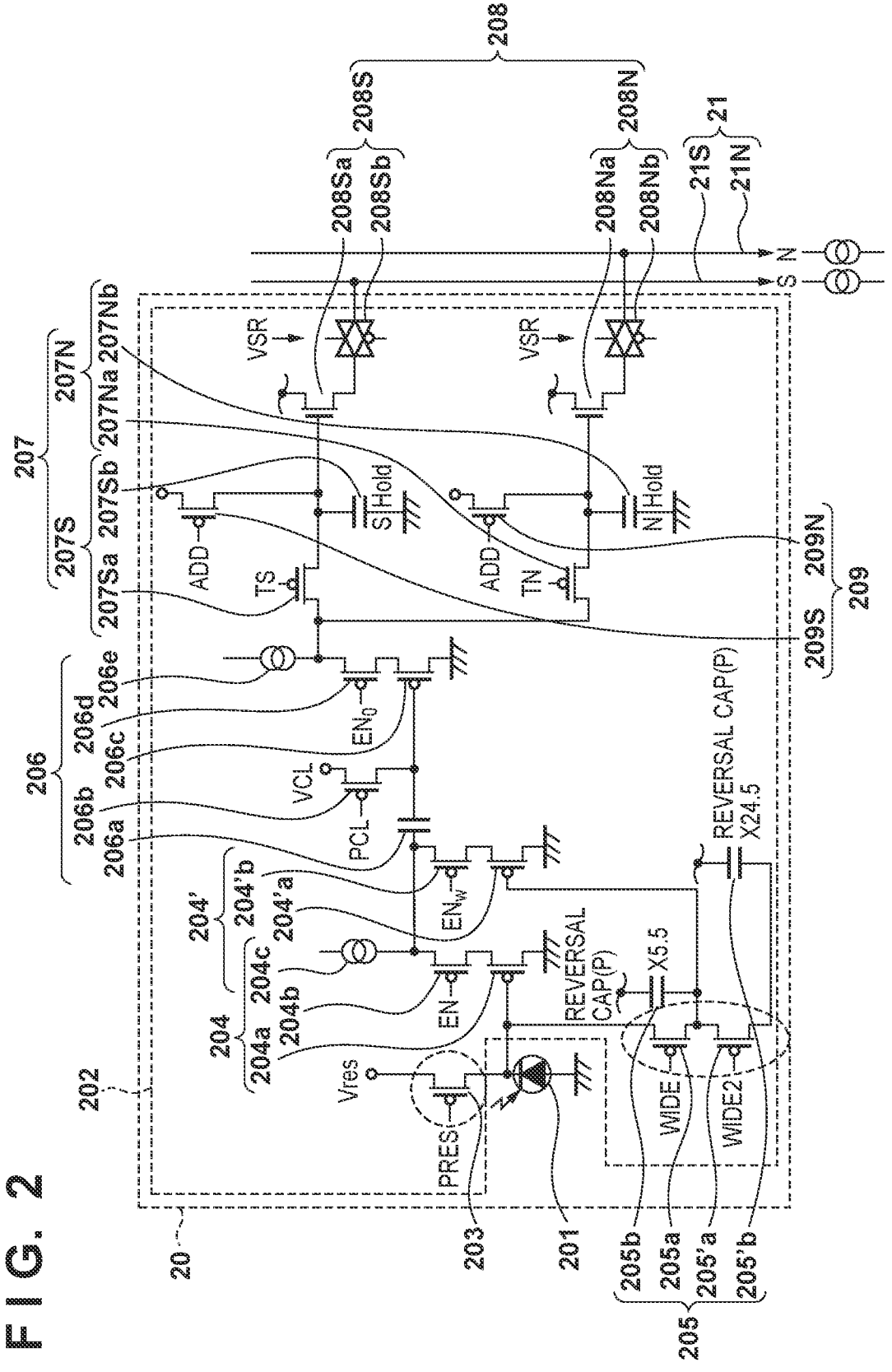

F I G. 3
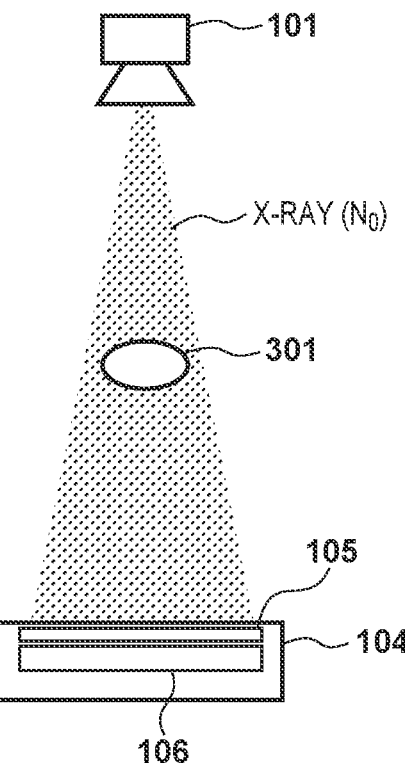

F I G. 4
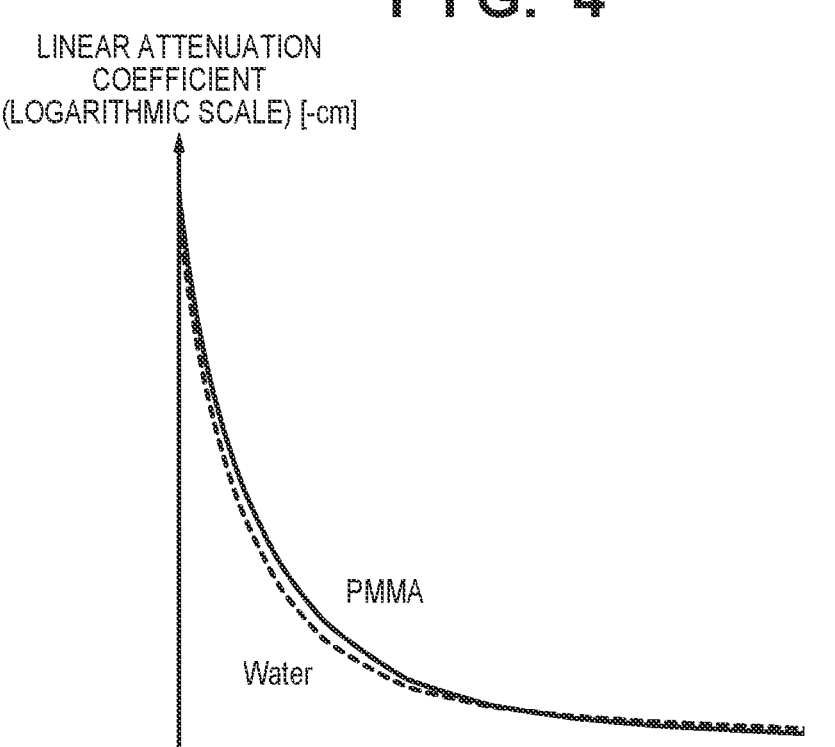
F I G. 5
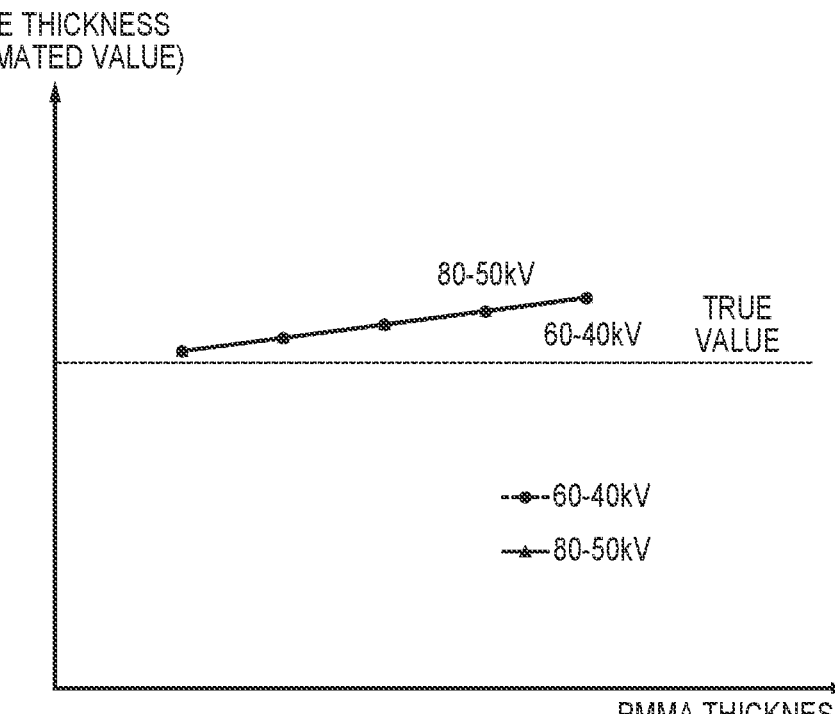

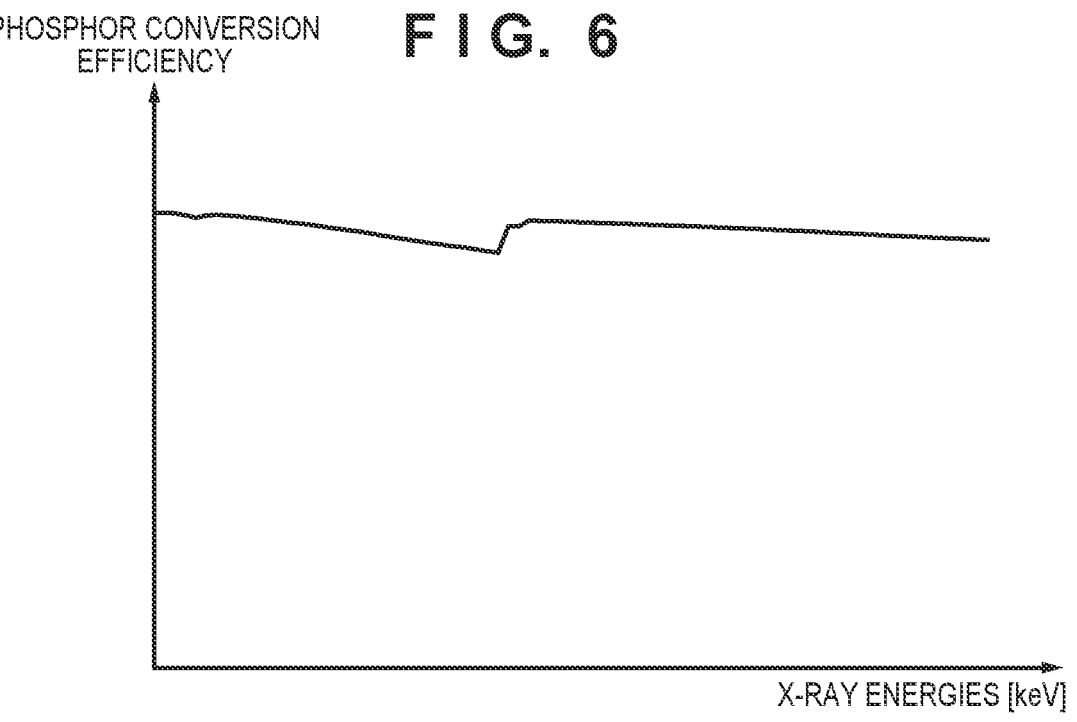
F I G. 6
PHOSPHOR CONVERSION
EFFICIENCY
X-RAY ENERGIES [keV]
F I G. 7
BONE THICKNESS
(ESTIMATED VALUE)
80-50kV
60-40kV
TRUE
VALUE
PMMA THICKNESS

F I G.  10
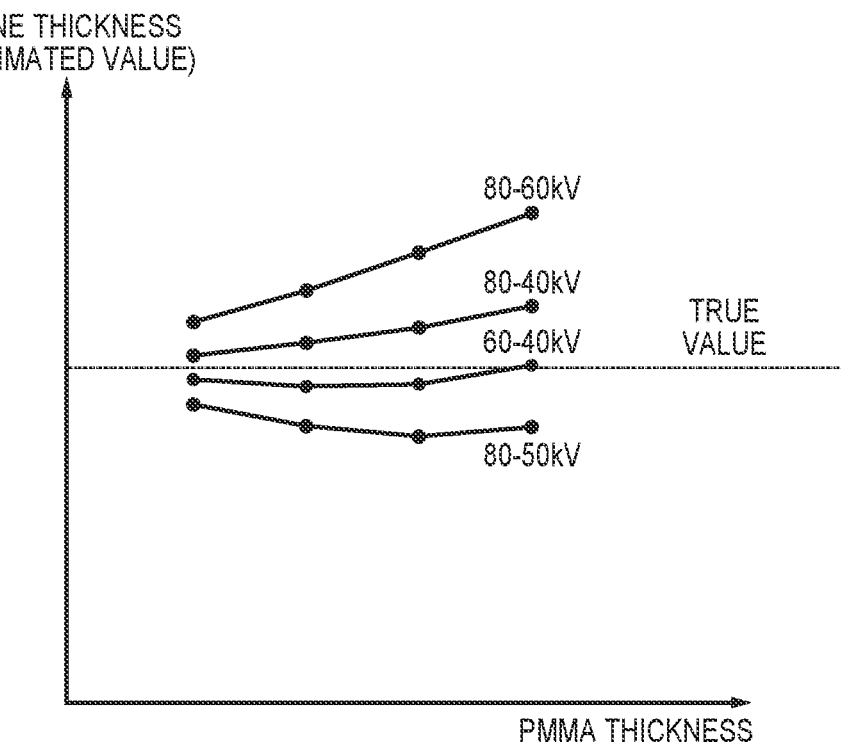
F I G.  11
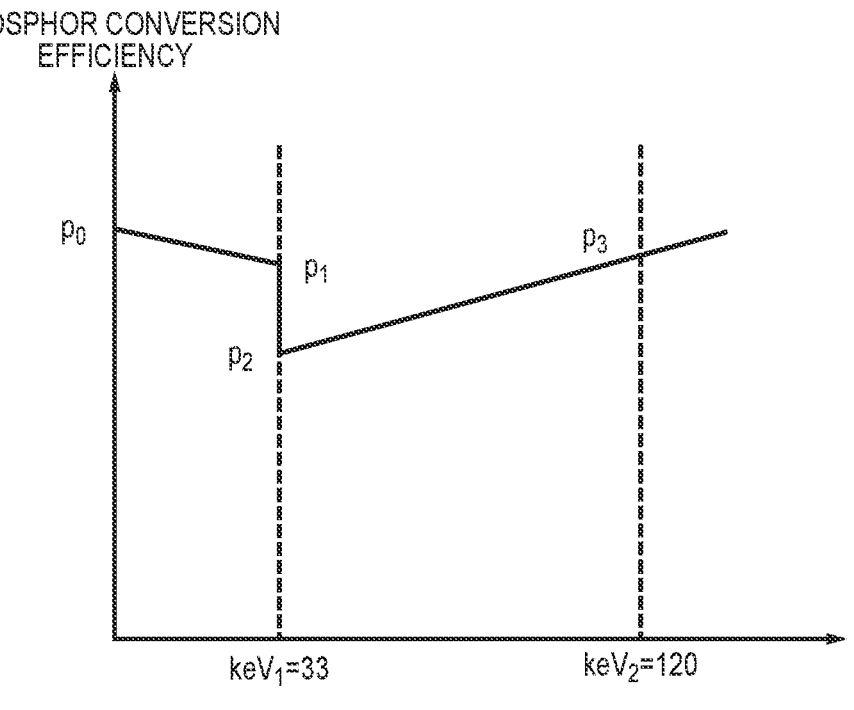

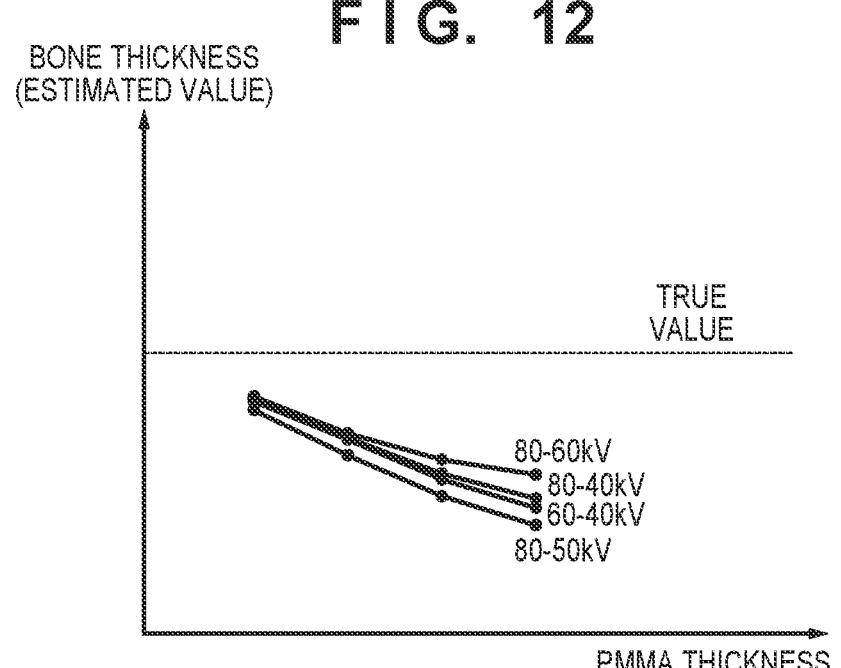
F I G. 12

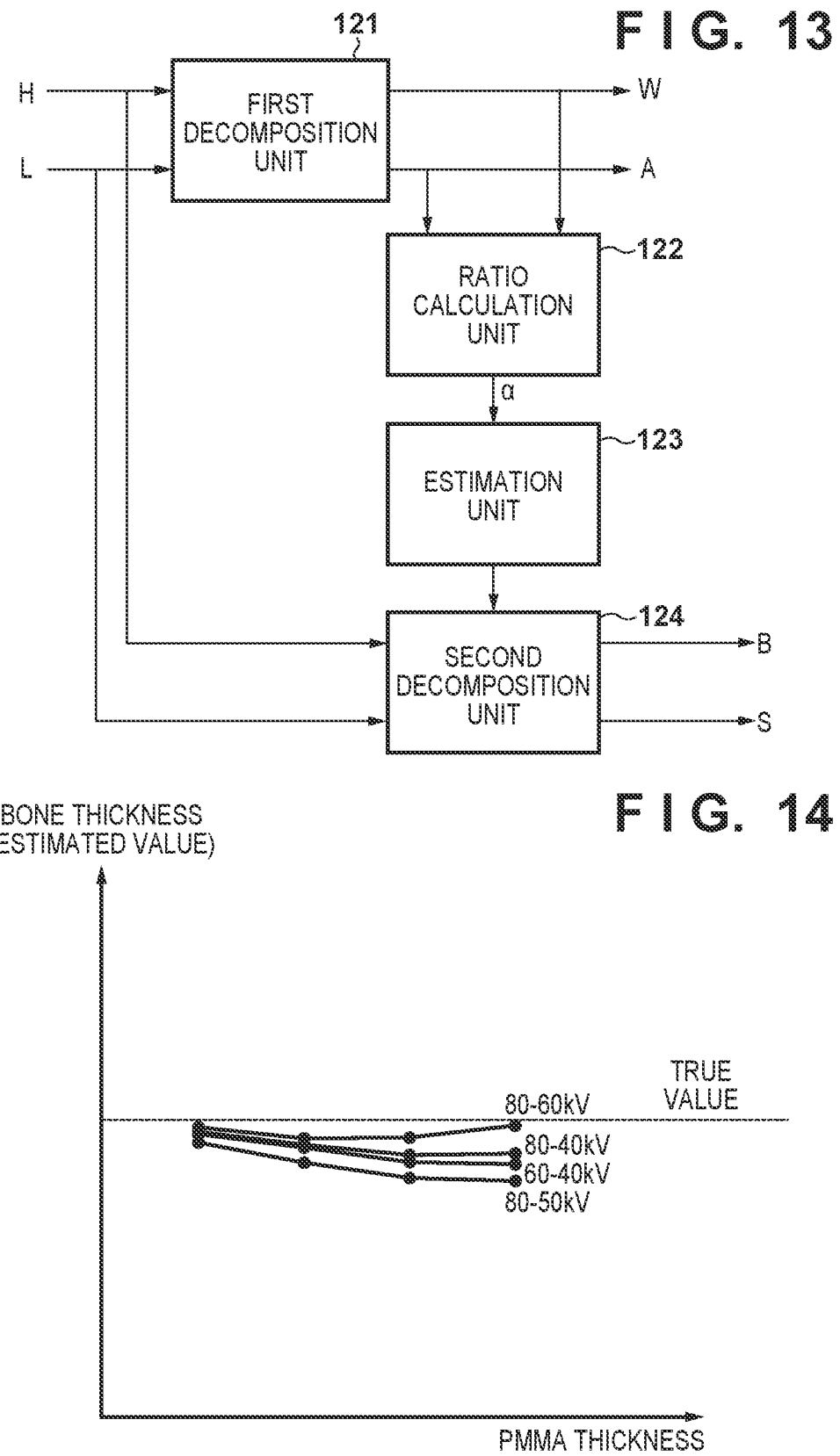
F I G. 13
F I G. 14

ENERGY SUBTRACTION PROCESSING APPARATUS, ENERGY SUBTRACTION PROCESSING METHOD, RADIATION IMAGING SYSTEM, AND NON-TRANSITORY COMPUTER-READABLE STORAGE MEDIUM

BACKGROUND OF THE INVENTION

Field of the Invention

The present disclosure relates to an information processing apparatus configured to process a radiation image, an information processing method, a radiation imaging system, and a non-transitory computer-readable storage medium.

Description of the Related Art

A radiation imaging apparatus using a flat panel detector (to be abbreviated as an FPD hereinafter) made of a semi-conductor material is currently widespread as an imaging apparatus used for medical image diagnosis or non-destructive inspection by X-rays. Such a radiation imaging apparatus is used as a digital imaging apparatus for still image capturing like general imaging or moving image capturing like fluoroscopic imaging in, for example, medical image diagnosis.

One of imaging methods using an FPD is energy subtraction processing. Japanese Patent Laid-Open No. 2019-162358 discloses processing of obtaining a plurality of radiation images of different energies by, for example, emitting X-rays of different tube voltages and decomposing (material-decomposing) a bone image and a soft tissue image from the plurality of radiation images. Also, Japanese Patent Laid-Open No. 2020-203083 discloses a technique of correcting an error included in a parameter used in energy subtraction processing (material decomposition).

SUMMARY OF THE INVENTION

According to one aspect of the present invention, there is provided an information processing apparatus comprising: a processing unit configured to obtain a plurality of results by performing energy subtraction processing for each of a plurality of sets which are sets each formed from a plurality of radiation images corresponding to different radiation energies and in which combinations of radiation energies are different; and a determination unit configured to determine a value of a predetermined parameter used in the energy subtraction processing such that a dispersion between the plurality of results is reduced.

Further features of the present invention will become apparent from the following description of exemplary embodiments with reference to the attached drawings.

BRIEF DESCRIPTION OF THE DRAWINGS

FIG. 2 is a view showing an example of the circuit configuration of a pixel in a two-dimensional detector;

FIG. 3 is a view for explaining the configuration of X-ray imaging according to the first embodiment;

FIG. 4 is a graph showing an example of a linear attenuation coefficient;

FIG. 5 is a graph showing a result of bone thickness estimation in a case where the linear attenuation coefficient includes an error;

FIG. 6 is a graph showing an example of a phosphor conversion efficiency;

FIG. 7 is a graph showing a result of bone thickness estimation in a case where the phosphor conversion efficiency includes an error;

FIG. 10 is a graph showing the results of bone thickness estimation for combinations of tube voltages;

FIG. 11 is a graph showing a model of the phosphor conversion efficiency according to the first embodiment;

FIG. 12 is a graph showing the results of bone thickness estimation for combinations of tube voltages after correction of the phosphor conversion efficiency;

FIG. 13 is a block diagram showing an example of the functional configuration of a control computer according to the second embodiment; and FIG. 14 is a graph showing the results of bone thickness estimation after correction processing according to the second embodiment.

DESCRIPTION OF THE EMBODIMENTS

Figure 1:
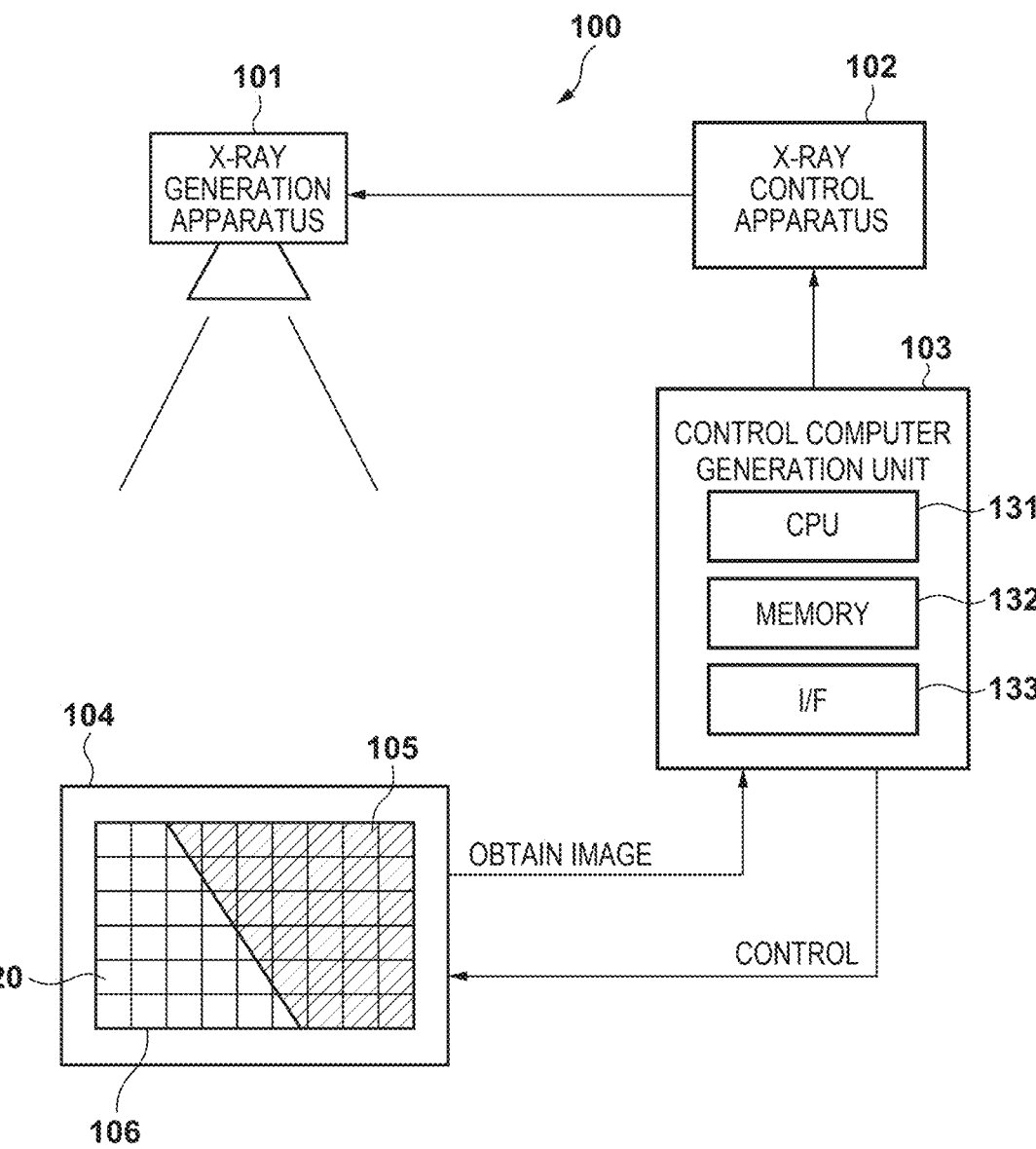
FIG. 1 is a view showing an example of the configuration of a radiation imaging apparatus according to the first embodiment.

The embodiments will now be described in detail with reference to the accompanying drawings. Note that the following embodiments do not limit the present disclosure according to the appended claims. A plurality of features are described in the embodiments. Not all the plurality of features are essential for the present disclosure, and the plurality of features can arbitrarily be combined. Also, the same reference numerals denote the same or similar parts in the accompanying drawings, and a repetitive description thereof will be omitted.

The following embodiments improve the accuracy of energy subtraction processing.

If a parameter used in energy subtraction processing includes an error, a deviation occurs between the result of energy subtraction processing and a true value. For example, when estimating a bone thickness and a soft tissue thickness using energy subtraction processing, an error is generated between the estimated value and the true value of each thickness. As the result of such an error, the accuracy of bone density measurement lowers, or an artifact occurs when image processing is applied to the estimated bone thickness or soft tissue thickness. In a conventional technique, correction is performed concerning an error factor such as the dose dependence of an attenuation rate, thereby improving the accuracy of energy subtraction processing. In general, however, if there are two or more error factors, parameter correction is difficult, and this impedes improving the accuracy of energy subtraction processing.

An information processing apparatus according to this embodiment performs energy subtraction processing for each of a plurality of sets which are sets each formed from a plurality of radiation images corresponding to different radiation energies and in which combinations of radiation energies are different, thereby obtaining a plurality of results. The information processing apparatus according to this embodiment then determines the value of a predetermined parameter used in the energy subtraction processing such that the dispersion between the plurality of results is reduced.

According to this embodiment, it is possible to improve the accuracy of energy subtraction processing.

Note that radiation in the disclosed technique includes not only α-rays, β-rays, and γ-rays that are beams generated by particles (including photons) emitted by radioactive decay but also beams having equal or more energy, for example, X-rays, particle rays, and cosmic rays. Note that in the following embodiments, X-rays are used as radiation.

First Embodiment

FIG. 1 is a block diagram showing an example of the configuration of a radiation imaging system according to the first embodiment. A radiation imaging system 100 according to this embodiment is suitably used for still image capturing like general imaging or moving image capturing like fluoroscopic imaging in medical diagnosis. The radiation imaging system 100 includes an X-ray generation apparatus 101, an X-ray control apparatus 102, a control computer 103, and an X-ray imaging apparatus 104. The X-ray generation apparatus 101 radiates X-rays under the control of the X-ray control apparatus 102. The control computer 103 is an information processing apparatus including, for example, a CPU 131 serving as a processor, and a memory 132. The control computer 103 is connected to the X-ray control apparatus 102 and the X-ray imaging apparatus 104 via an interface (UF 133) and performs various kinds of control in the radiation imaging system. The X-ray imaging apparatus 104 is formed by a phosphor 105 that converts X-rays into visible light, and a two-dimensional detector 106 that detects the visible light. The two-dimensional detector 106 is a sensor in which pixels 20 configured to detect X-ray quanta are arranged in an array of X columns×Y rows, and outputs image information (radiation image).

FIG. 2 shows an equivalent circuit diagram of the pixel 20 included in the two-dimensional detector 106 according to the first embodiment. The pixel 20 includes a photoelectric conversion element 201 and an output circuit unit 202. The photoelectric conversion element 201 can typically be a photodiode. The output circuit unit 202 includes an amplification circuit unit 204, a clamp circuit unit 206, a sample and hold circuit unit 207, and a selection circuit unit 208.

The photoelectric conversion element 201 includes a charge accumulation portion. The charge accumulation portion is connected to the gate of a MOS transistor 204a of the amplification circuit unit 204. The source of the MOS transistor 204a is connected to a current source 204c via a MOS transistor 204b. The MOS transistor 204a and the current source 204c form a source follower circuit. The MOS transistor 204b is an enable switch that is turned on when an enable signal EN supplied to its gate is set at an active level, and sets the source follower circuit in an operation state.

In the example shown in FIG. 2, the charge accumulation portion of the photoelectric conversion element 201 and the gate of the MOS transistor 204a form a common node, and this node functions as a charge-voltage converter that converts charges accumulated in the charge accumulation portion into a voltage. That is, a voltage V (=Q/C) determined by charges Q accumulated in the charge accumulation portion and a capacitance value C of the charge-voltage converter appears in the charge-voltage converter. The charge-voltage converter is connected to a reset potential Vres via a reset switch 203. When a reset signal PRES is set at an active level, the reset switch 203 is turned on, and the potential of the charge-voltage converter is reset to the reset potential Vres.

The clamp circuit unit 206 clamps, by a clamp capacitor 206a, noise output from the amplification circuit unit 204 in accordance with the reset potential of the charge-voltage converter. That is, the clamp circuit unit 206 is a circuit configured to cancel the noise from a signal output from the source follower circuit in accordance with charges generated by photoelectric conversion in the photoelectric conversion element 201. The noise includes kTC noise at the time of reset. Clamping is performed by turning on a MOS transistor 206b by setting a clamp signal PCL at an active level, and then turning off the MOS transistor 206b by setting the clamp signal PCL at an inactive level. The output side of the clamp capacitor 206a is connected to the gate of a MOS transistor 206c. The source of the MOS transistor 206c is connected to a current source 206e via a MOS transistor 206d. The MOS transistor 206c and the current source 206e form a source follower circuit. The MOS transistor 206d is an enable switch that is turned on when an enable signal ENO supplied to its gate is set at an active level, and sets the source follower circuit in an operation state.

The signal output from the clamp circuit unit 206 in accordance with charges generated by photoelectric conversion in the photoelectric conversion element 201 is written, as an optical signal, in a capacitor 207Sb via a switch 207Sa when an optical signal sampling signal TS is set at an active level. The signal output from the clamp circuit unit 206 when turning on the MOS transistor 206b immediately after resetting the potential of the charge-voltage converter is a clamp voltage. The noise signal is written in a capacitor 207Nb via a switch 207Na when a noise sampling signal TN is set at an active level. This noise signal includes an offset component of the clamp circuit unit 206. The switch 207Sa and the capacitor 207Sb form a signal sample and hold circuit 207S, and the switch 207Na and the capacitor 207Nb form a noise sample and hold circuit 207N. The sample and hold circuit unit 207 includes the signal sample and hold circuit 207S and the noise sample and hold circuit 207N.

When a driving circuit unit drives a row selection signal to an active level, the signal (optical signal) held in the capacitor 207Sb is output to a signal line 21S via a MOS transistor 208Sa and a row selection switch 208Sb. In addition, the signal (noise) held in the capacitor 207Nb is simultaneously output to a signal line 21N via a MOS transistor 208Na and a row selection switch 208Nb. The MOS transistor 208Sa forms a source follower circuit with a constant current source (not shown) provided on the signal line 21S. Similarly, the MOS transistor 208Na forms a source follower circuit with a constant current source (not shown) provided on the signal line 21N. The MOS transistor 208Sa and the row selection switch 208Sb form a signal selection circuit unit 208S, and the MOS transistor 208Na and the row selection switch 208Nb form a noise selection circuit unit 208N. The selection circuit unit 208 includes the signal selection circuit unit 208S and the noise selection circuit unit 208N.

The pixel 20 may include an addition switch 209S that adds the optical signals of the plurality of adjacent pixels 20. In an addition mode, an addition mode signal ADD is set at an active level, and the addition switch 209S is turned on. This causes the addition switch 209S to interconnect the capacitors 207Sb of the adjacent pixels 20, and the optical signals are averaged. Similarly, the pixel 20 may include an addition switch 209N that adds noise components of the plurality of adjacent pixels 20. When the addition switch 209N is turned on, the capacitors 207Nb of the adjacent pixels 20 are interconnected by the addition switch 209N, thereby averaging the noise components. An adder 209 includes the addition switches 209S and 209N.

Furthermore, the pixel 20 may include a sensitivity changing unit 205 for changing the sensitivity. The pixel 20 can include, for example, a first sensitivity change switch 205a, a second sensitivity change switch 205'a, and their circuit elements. When a first change signal WIDE is set at an active level, the first sensitivity change switch 205a is turned on to add the capacitance value of a first additional capacitor 205b to the capacitance value of the charge-voltage converter. This decreases the sensitivity of the pixel 20. When a second change signal WIDE2 is set at an active level, the second sensitivity change switch 205'a is turned on to add the capacitance value of a second additional capacitor 205'b to the capacitance value of the charge-voltage converter. This further decreases the sensitivity of the pixel 20. In this way, it is possible to receive a larger light amount by adding a function of decreasing the sensitivity of the pixel 20, thereby widening a dynamic range. When the first change signal WIDE is set at the active level, an enable signal ENw may be set at an active level to cause a MOS transistor 204'a to perform a source follower operation instead of the MOS transistor 204a.

The X-ray imaging apparatus 104 reads out the output of the pixel circuit as described above, obtains a radiation image by causing an A/D converter (not shown) to convert the output into a digital value, and transfers the radiation image to the control computer 103.

Energy subtraction processing will be described next. Let E be energy of X-ray photons, N(E) be an X-ray spectrum, C(E) be a phosphor conversion efficiency, D be the thickness of an object that is an arbitrary material, and $\mu(E)$ be the linear attenuation coefficient of an object 301. An attenuation rate image $I/I_0$ is represented by equation (1) below. In this embodiment, such an attenuation rate image is used as a radiation image (X-ray image) in energy subtraction processing. Here, the phosphor conversion efficiency C(E) means the ratio of X-rays contributing to a pixel value in X-rays that are not transmitted through the phosphor.

$$I/I_0 = \frac{\int_0^\infty C(E)N(E)\exp\{-\mu(E)D\}EdE}{\int_0^\infty C(E)N(E)EdE} \tag{1}$$

FIG. 3 is a view schematically showing X-ray imaging by the radiation imaging system according to this embodiment. The object 301 is arranged between the X-ray generation apparatus 101 and the X-ray imaging apparatus 104. Letting $N_0(E)$ be the spectrum of X-rays radiated from the X-ray generation apparatus 101 at the energy E, $\mu_C(E)$ be the linear attenuation coefficient of the phosphor 105 at the energy E, $d_C$ be a thickness, and $P_C$ be a filling rate, equation (2) below holds. Note that for the sake of simplicity, phosphor conversion efficiency C(E)=1 is assumed.

$$N(E)=N_0(E)[1-\exp\{-\mu_C(E)d_CP_C\}] \tag{2}$$

The X-ray spectrum N of equation (2) is a spectrum considering X-ray absorption of the phosphor 105 and is obtained from the X-ray spectrum $N_0(E)$ and a parameter concerning the X-ray absorption of the phosphor 105. The X-ray spectrum $N_0(E)$ is obtained by a simulation or actual measurement. Also, the phosphor conversion efficiency $\mu_C(E)$ of the phosphor 105 at the energy E, the thickness $d_C$, and the filling rate $P_C$ are obtained from design values, respectively. Furthermore, the linear attenuation coefficient $\mu(E)$ of the object 301 at the energy E is obtained from the database of the NIST or the like. Hence, the attenuation rate $I/I_0$ of the object 301 having a thickness D at the X-ray spectrum N(E) can be calculated from equations (1) and (2).

A method of calculating the image of the thickness of an object formed from only a bone and the image of the thickness of an object formed from only a soft tissue from an attenuation rate image H at high energy and an attenuation rate image L at low energy by energy subtraction processing will be described next. Letting B the bone thickness, S be the soft tissue thickness, $\mu_B(E)$ be the linear attenuation coefficient of the bone at the energy E, $\mu_S(E)$ be the linear attenuation coefficient of the soft tissue, $N_L(E)$ be the X-ray spectrum at a low tube voltage, and $N_H(E)$ be the X-ray spectrum at a high tube voltage, equations (3) below hold.

$$H = \frac{\int_0^\infty C(E)N_H(E)\exp\{-\mu_B(E)B - \mu_S(E)S\}EdE}{\int_0^\infty C(E)N_H(E)EdE} \tag{3}$$

$$L = \frac{\int_0^\infty C(E)N_L(E)\exp\{-\mu_B(E)B - \mu_S(E)S\}EdE}{\int_0^\infty C(E)N_L(E)EdE}$$

By solving nonlinear simultaneous equations (3), the bone thickness B and the soft tissue thickness S can be obtained. Hence, when equations (3) are calculated for all pixels, the bone thickness image B and the soft tissue thickness image S can be obtained from the attenuation rate image L at low energy and the attenuation rate image H at high energy. Processing of decomposing images of two types of physical quantities like a bone and a soft tissue from images captured at different radiation energies (in this example, X-ray energies) will be referred to as material decomposition hereinafter.

Note that as the solution to equations (3), a known method, for example, an iterative method such as the Newton-Raphson method, the least squares method, or the bisection method can be used. Alternatively, a table may be generated by obtaining the bone thicknesses B and the soft tissue thicknesses S corresponding to various combinations of attenuation rates H at high energy and attenuation rates L at low energy in advance, and the solution of equations (3) may be obtained by referring to the table. When the solution of equations (3) is obtained by referring to such a table, the bone thickness B and the soft tissue thickness S can more quickly be obtained (see Japanese Patent Laid-Open No. 2020-203083).

The bone thickness B or the soft tissue thickness S obtained by solving equations (3) is called the calculated value (or estimated value) of the thickness. A thickness actually measured using a ruler or the like is called the true value of the thickness. If correction and signal processing are appropriately performed, the calculated value of the thickness matches the true value. However, the present inventor made examinations and found that the calculated value of the thickness did not necessarily match the true value. If the error between the calculated value of the thickness and the true value is large, an artifact occurs in the image after image processing.

The present inventor made examinations and found that if an error occurs in the attenuation rate images H and L on the left-hand side of equations (3) due to scattered rays or nonlinearity of the pixel 20, an erase residue may occur. Note that the erase residue means, for example, a phenomenon that the thickness of a soft tissue remains in a bone thickness image, or a phenomenon that the thickness of a bone remains in a soft tissue thickness image. It was also found that an erase residue occurs even in a case where the X-ray spectrum $N_L(E)$ at low energy, the X-ray spectrum $N_H(E)$ at high energy, and the phosphor conversion efficiency $C(E)$ on the right-hand side of equations (3) are different from actual values. Similarly, it was also found that an erase residue occurs even in a case where the linear attenuation coefficient $\mu_B(E)$ of the bone and the linear attenuation coefficient $\mu_S(E)$ of the soft tissue are different from actual linear attenuation coefficients. In the first embodiment, a method of correcting the error of the phosphor conversion efficiency $C(E)$ (independently of the linear attenuation coefficient) if an error caused by two error factors, that is, the linear attenuation coefficient and the phosphor conversion efficiency, are included in a measured value will be described. Note that for the sake of simplicity of the description, assume that scattered rays, the nonlinearity of the pixel 20, and the error of spectra are already removed or corrected.

In general, if there are two error factors, it is difficult to correct the error factors based on a calculated value and a true value. The present inventor earnestly examined the two error factors, the linear attenuation coefficient and the phosphor conversion efficiency, and obtained the following findings.

Even if the linear attenuation coefficient includes an error, the bone thicknesses B obtained by performing material decomposition for a plurality of sets each including a plurality of X-ray images captured at different tube voltages (the combinations of the tube voltages of the plurality of sets are different) substantially match.

If the phosphor conversion efficiency includes an error, the bone thicknesses B obtained by performing material decomposition for the plurality of sets do not match.

FIG. 4 shows examples of the linear attenuation coefficients of PMMA (Poly Methyl Methacrylate: acryl) and water. In FIG. 4, the linear attenuation coefficient of PMMA is indicated by a solid line, and the linear attenuation coefficient of water is indicated by a broken line. As shown in FIG. 4, each linear attenuation coefficient takes a different value for each energy of X-rays. If an error exists between the actual linear attenuation coefficient and the linear attenuation coefficient used as a parameter of energy subtraction processing, an error occurs in the bone thickness B obtained by material decomposition. FIG. 5 shows the bone thickness B obtained by material-decomposing PMMA for each of a plurality of sets of X-ray images captured at different tube voltages in a case where the linear attenuation coefficient includes an error. FIG. 5 shows the bone thicknesses B obtained for a set of X-ray images captured at tube voltages of 60 kV and 40 kV and a set of X-ray images captured at tube voltages of 80 kV and 50 kV. Since the object is only PMMA, the true value of the bone thickness is 0 regardless of the thickness. However, since the linear attenuation coefficient includes an error, the calculated value of the bone thickness B as the result of material decomposition includes an error to the true value. Note that although the bone thickness B never becomes less than 0 in actuality, a negative calculated value is obtained in calculation (because of an error of the parameter). It is considered that the calculated value of the bone thickness B is smaller than the true value (=0) because the thickness of the soft tissue is calculated thicker than actuality. On the other hand, it is found that between the plurality of sets of X-ray images, even if the linear attenuation coefficient includes an error, the results of material decomposition (the calculated values of the bone thickness B) substantially match for PMMA of the same thickness.

FIG. 6 shows an example of the phosphor conversion efficiency. As shown in FIG. 6, the phosphor conversion efficiency takes a different value for each energy, like the linear attenuation coefficient. If an error exists between the actual phosphor conversion efficiency and the phosphor conversion efficiency used as a parameter of energy subtraction processing, an error occurs in the bone thickness B obtained by material decomposition. FIG. 7 shows the bone thickness B obtained by material-decomposing PMMA for a plurality of sets of X-ray images in a case where the phosphor conversion efficiency includes an error. The combinations of tube voltages in each set are the same as in FIG. 5. If the phosphor conversion efficiency includes an error, the bone thickness B includes an error to the true value, like the case where the linear attenuation coefficient includes an error. Also, if the phosphor conversion efficiency includes an error, the decomposition results (bone thicknesses B) obtained for the sets do not match, unlike the case where the linear attenuation coefficient includes an error.

As described above, even if the linear attenuation coefficient includes an error, the deviation between the decomposition results obtained for different combinations of X-ray energies is small. If the phosphor conversion efficiency includes an error, the deviation between the decomposition results is large. It is therefore considered that by correcting the phosphor conversion efficiency such that the difference between a plurality of results obtained by energy subtraction processing using a plurality of sets becomes small, correction of the phosphor conversion efficiency can be performed without considering the influence of the error of the linear attenuation coefficient.

Figure 8:
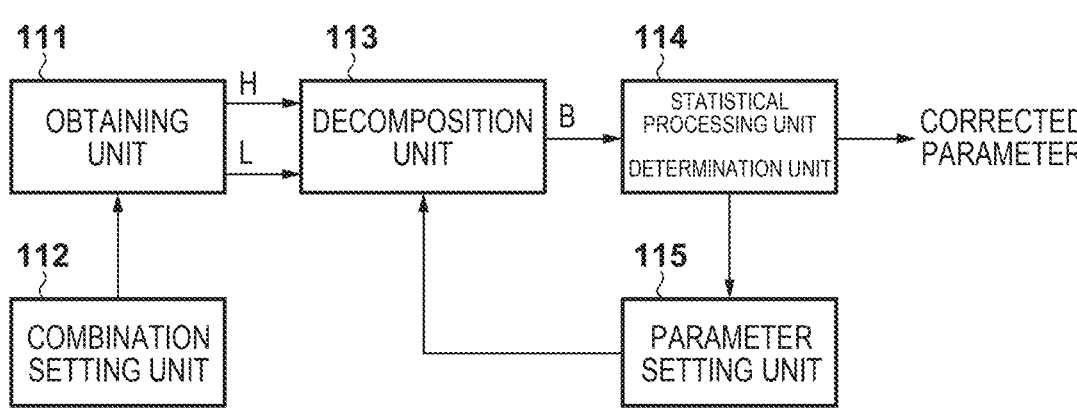
FIG. 8 is a block diagram showing an example of the functional configuration of a control computer according to the first embodiment.

Correction processing of the phosphor conversion efficiency according to the first embodiment will be described below. In this embodiment, the phosphor conversion efficiency is corrected by generating, in place of a phosphor conversion efficiency as shown in FIG. 6, a linear model of a phosphor conversion efficiency (to be described later with reference to FIG. 11) such that the influence of the error of the phosphor conversion efficiency on two-material decomposition is reduced. FIG. 8 is a block diagram showing an example of a functional configuration for correction processing of the phosphor conversion efficiency according to the first embodiment. Each functional block can be implemented by the CPU 131 of the control computer 103 executing a predetermined program stored in the memory 132. However, each functional block may be implemented by dedicated hardware or may be implemented by cooperation of the CPU 131 and hardware.

An obtaining unit 111 obtains three or more radiation images captured using the X-ray control apparatus 102 and the X-ray imaging apparatus 104 using a plurality of radiation rays whose energies are different from each other. In the above-described example, four X-ray images captured using X-rays of four tube voltages of 80, 60, 50, and 40 kV, that is, X-rays of four different energies are obtained. A combination setting unit 112 sets a plurality of sets each formed by a plurality of radiation images of the three or more radiation images obtained by the obtaining unit 111 and corresponding to a different energy combination. In the above-described example, four sets (80-60 kV, 80-40 kV, 60-40 kV, and 80-50 kV) each formed by a combination of two radiation images are selected from the four radiation images. Note that the plurality of tube voltages obtained by the obtaining unit 111, as described above, and the combinations of tube voltages set by the combination setting unit 112 may be instructed by the user.

A parameter setting unit 115 provides parameters (including a predetermined parameter that is a correction target) to be used in energy subtraction processing to a decomposition unit 113. The decomposition unit 113 performs energy subtraction processing using the parameters provided by the parameter setting unit 115 for each of the plurality of sets set by the combination setting unit 112. A statistical processing unit 114 calculates a statistic concerning the dispersion of a plurality of results (for example, the bone thicknesses B) of energy subtraction processing obtained from the decomposition unit 113 for the plurality of sets. The parameter setting unit 115 changes the predetermined parameter and sets it to the decomposition unit 113. Every time the predetermined parameter is changed, the decomposition unit 113 provides a plurality of results obtained for the plurality of sets to the statistical processing unit 114. The statistical processing unit 114 determines the predetermined parameter obtained when the calculated dispersion becomes small (in this example, the dispersion is minimized) to a corrected parameter. Thus, the predetermined parameter used in energy subtraction processing is corrected such that the dispersion of the results (bone thicknesses B) of energy subtraction processing is reduced. A description will be made below using, as an example, a case where the predetermined parameter as the correction target is the phosphor conversion efficiency.

Figure 9:
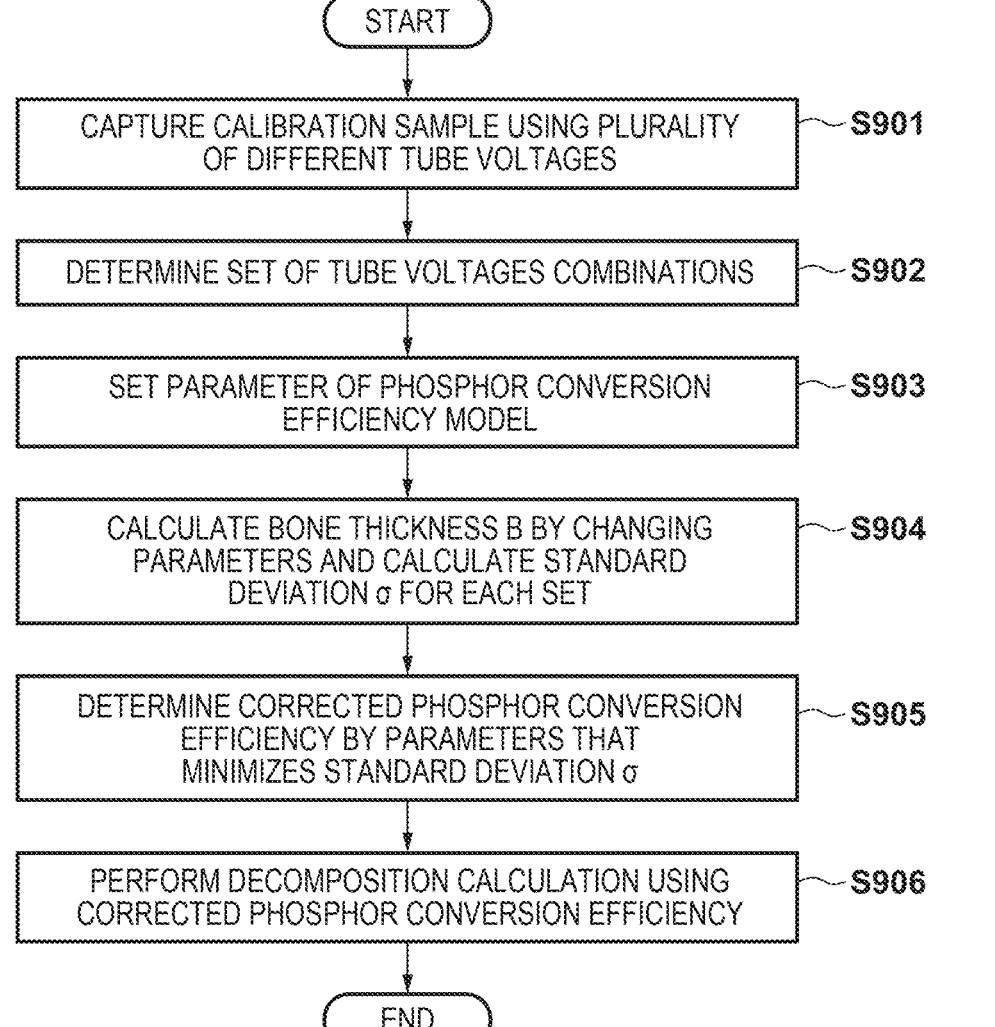
FIG. 9 is a flowchart showing correction processing of the phosphor conversion efficiency according to the first embodiment.

FIG. 9 is a flowchart showing correction processing of the phosphor conversion efficiency according to this embodiment. First, the obtaining unit 111 captures a calibration sample (in this example, PMMA) using a plurality of different tube voltages (in this example, 80, 60, 50, and 40 kV), thereby obtaining X-ray images captured at a plurality of energies (step S901). Next, the combination setting unit 112 sets a plurality of sets each formed from a plurality of X-ray images obtained using the different tube voltages (step S902). For example, the combination setting unit 112 sets X-ray image sets corresponding to four combinations 80-40 kV, 80-50 kV, 80-60 kV, and 60-40 kV. FIG. 10 shows the calculation results of the bone thickness B obtained by the decomposition unit 113 by performing energy subtraction processing for each of the four sets at the time of examinations by the present inventor. Since the phosphor conversion efficiency includes an error, the bone thicknesses B obtained using energy subtraction processing for the sets do not match.

Next, the statistical processing unit 114 and the parameter setting unit 115 correct the phosphor conversion efficiency such that the difference of the bone thickness B between the tube voltage combinations becomes small. More specifically, the phosphor conversion efficiency is modelled such that a standard deviation σ (equation (4) below) of the bone thicknesses B becomes small. Note that in equation (4), n represents the number of data; $B_i$, the bone thickness of ith data; and B⁻, the average value of bone thicknesses (the average value of bone thicknesses $B_1$ to $B_n$).

$$\sigma = \sqrt{\frac{1}{n}\sum_{i=1}^{n}(B_i - \bar{B})^2} \qquad (4)$$

For the phosphor conversion efficiency C(E), a linear model as shown in FIG. 11 is assumed. This is a model created based on the assumption that there is the influence of k-edge. In this embodiment, a linear model defined by six parameters $keV_1$, $keV_2$, $p_0$, $p_1$, $p_2$, and $p_3$ as shown in FIG. 11 is used. Equation (5) is an equation representing the model of the phosphor conversion efficiency C(E).

$$C(E) = \begin{cases} \dfrac{p_1 - p_0}{keV_1}E + p_0 & (E < keV_1) \\ \dfrac{(p_3 - p_2)E - p_3keV + p_2keV_2}{keV_2 - keV_1} & (E \geq keV_1) \end{cases} \qquad (5)$$

The parameter setting unit 115 sets a parameter set used to model the phosphor conversion efficiency into a linear model as shown in FIG. 11 (step S903). In this example, assuming the influence of k-edge, the parameter setting unit 115 fixes $keV_1$=33 and also fixes $keV_2$=120. The parameter setting unit 115 changes the remaining four parameters ($p_0$, $p_1$, $p_2$, and $p_3$) to various values, thereby obtaining a plurality of parameter sets concerning the linear model of the phosphor conversion efficiency. The decomposition unit 113 performs energy subtraction processing using the model of the phosphor conversion efficiency represented by each of the plurality of parameter sets, thereby calculating the bone thickness B. Using the bone thickness B obtained from the decomposition unit 113, the statistical processing unit 114 calculates the standard deviation σ by equation (4) (step S904). The statistical processing unit 114 then determines the model of the phosphor conversion efficiency represented by the parameter set that minimizes the standard deviation σ calculated in step S904 to the corrected phosphor conversion efficiency (step S905). By steps S901 to S905 described above, the plurality of parameters ($p_0$, $p_1$, $p_2$, and $p_3$) for specifying the model of the phosphor conversion efficiency are determined. The value of the parameter (the value C(E) in equations (3)) used in subsequent energy subtraction processing is determined from this model.

The control computer 103 performs energy subtraction processing (material decomposition) using the phosphor conversion efficiency (linear model) corrected in the above-described way (step S906). That is, the control computer 103 obtains a plurality of X-ray images of a diagnosis target object corresponding to a plurality of X-ray energies, which are captured by the X-ray imaging apparatus 104. Then, the control computer 103 performs energy subtraction processing for the plurality of X-ray images using the phosphor conversion efficiency determined by the processing in steps S901 to S905, thereby generating an image to be used for diagnosis. FIG. 12 shows the bone thicknesses B that the present inventor estimated by energy subtraction processing using the phosphor conversion efficiency corrected by the above-described method. It is found that the difference between the results of the bone thicknesses B for the tube voltage combinations can be made small. Note that the processing in steps S901 to S905 (processing of determining the phosphor conversion efficiency) need not be performed in every image capturing of the object, and executing the process at an appropriate interval (for example, one month) suffices. The processing is preferably executed when, for example, the X-ray imaging apparatus 104 is exchanged.

Note that in this embodiment, to correct the phosphor conversion efficiency, the bone thickness B and the soft tissue thickness S are calculated for the plurality of sets of X-ray images. However, the disclosed technique is not limited to this form, and an image may be decomposed into the thicknesses of arbitrary two types of materials. For example, a water thickness W and a contrast agent thickness I may be calculated in place of the bone thickness B and the soft tissue thickness S. Also, in place of the thicknesses of materials, an image of an effective atomic number Z and an image of a surface density D may be obtained from the attenuation rate image H at high energy and the attenuation rate image L at low energy represented by equations (3). The effective atomic number Z is an equivalent atomic number of a mixture, and the surface density D is the product of the density [g/cm$^3$] of an object and the thickness [cm] of the object. Furthermore, a virtual monochromatic X-ray image may be generated using the effective atomic number Z and the surface density D. Also, a combined X-ray image may be generated by combining a plurality of virtual monochromatic X-ray images generated using a plurality of energies [E$_V$]. The combined X-ray image is an image assumed to be obtained by irradiation of X-rays of an arbitrary spectrum.

Also, the bone thickness B is used as the index of correction of the phosphor conversion efficiency. However, the present invention is not limited to this. For example, the soft tissue thickness S may be used as the index. Alternatively, in the combination of the water thickness W and the contrast agent thickness I, an arbitrary one of these may be used as the index of correction of the parameter. One index of the effective atomic number Z and the surface density D may be used. In addition, these may be combined. That is, as the index of correction, an arbitrary image generated by energy subtraction processing can be used. As the set of tube voltages, a set of tube voltages selected from 80, 60, 50, and 40 kV is used. However, the present invention is not limited to this, as a matter of course. A combination of tube voltages other than those shown in the embodiment may be used, or radiation quality may freely be selected using a filter or the like. In addition, the standard deviation is used as the index of the difference of the results of energy subtraction processing. However, the present invention is not limited to this. Another statistic such as a variance may be used. Also, in this embodiment, the phosphor conversion efficiency C(E) is corrected assuming a model that combines linear functions. However, the present invention is not limited to this. Correction may be performed assuming a model using a quadratic function, a natural logarithm, or a combination thereof. In the above description, the phosphor conversion efficiency is determined such that σ is minimized for one PMMA thickness. However, the present invention is not limited to this, and the phosphor conversion efficiency may be determined based on σ obtained for a plurality of PMMA thicknesses. For example, the phosphor conversion efficiency may be determined such that the sum (average) of σ obtained for a plurality of PMMA thicknesses as shown in FIG. 10 or 12 is minimized. To search for an appropriate combination of parameters of the model shown in FIG. 10, grid search may be used. Grid search is a known method for searching for a parameter of a model, and grid search can obviously be used to search for a combination of parameters of the model shown in FIG. 10 such that the standard deviation σ is minimized.

As described above, according to the first embodiment, when the phosphor conversion efficiency is determined such that the results of energy subtraction processing for different tube voltages match, the phosphor conversion efficiency can be corrected even if an error is included in the linear attenuation coefficient.

Second Embodiment

In the first embodiment, a method of making results for different tube voltage combinations match by correcting the phosphor conversion efficiency has been described. In the second embodiment, a case where not only the phosphor conversion efficiency but also the error of the linear attenuation coefficient is corrected will be described.

As shown in FIG. 12, in the first embodiment, when the phosphor conversion efficiency is corrected, the difference between bone thicknesses B for the different tube voltage combinations becomes small. On the other hand, since an error exists in the linear attenuation coefficient, the bone thickness B does not match the true value. In the second embodiment, after the correction of the phosphor conversion efficiency described in the first embodiment is performed, the linear attenuation coefficient of the soft tissue is adjusted. More specifically, a control computer 103 captures a calibration object using an X-ray generation apparatus 101 and an X-ray imaging apparatus 104, and adjusts the linear attenuation coefficient of the object based on the ratio of water and the soft tissue in decomposition. Details will be described below.

FIG. 13 is a block diagram showing an example of the functional configuration of signal processing in the control computer 103 according to the second embodiment. A first decomposition unit 121 performs material decomposition using an attenuation rate image H at high energy and an attenuation rate image L at low energy as in the method described in the first embodiment. As in the first embodiment, PMMA can be used as an object 301. However, the first decomposition unit 121 obtains a water image W representing a water thickness and a fat image A representing a fat thickness using a linear attenuation coefficient $\mu_W(E)$ of water and a linear attenuation coefficient $\mu_A(E)$ of fat. A ratio calculation unit 122 calculates a ratio $\alpha=w/(w+a)$ of water contained in the soft tissue from the water image W and the fat image A obtained by the first decomposition unit 121. Here, for example, the average of calculated values of the water thickness [cm] obtained from the water image W in a region of interest (ROI) can be used as w. In addition, the average of calculated values of the fat thickness [cm] obtained from the fat image A in the ROI can be used as a. Note that the sum of thicknesses (corresponding to a volume) in the ROI may be used as each of w and a. As the ROI, for example, an arbitrary region including the object 301 can be used. The ROI may be designated by the user.

From the ratio α of water contained in the soft tissue obtained by the ratio calculation unit 122, an estimation unit 123 estimates (adjusts) a linear attenuation coefficient $\mu_S(E)$ of the soft tissue by equation (6) below.

$$\mu_S(E)=\alpha\mu_w(E)+(1-\alpha)\mu_A(E) \tag{6}$$

A second decomposition unit 124 obtains a bone image B and a soft tissue image S using the linear attenuation coefficient $\mu_S(E)$ of the soft tissue estimated by the estimation unit 123. When such processing is performed, the error between the actual linear attenuation coefficient of the soft tissue and the linear attenuation coefficient $\mu_S(E)$ of the soft tissue to be input to signal processing becomes small, and the accuracy of the embodiment bone thickness B can be increased.

The present inventor made examinations and found that if the linear attenuation coefficient is adjusted by the above-described method, the difference of the bone thickness B obtained between the above-described plurality of sets of images becomes large in some cases. In this embodiment, the correction of the phosphor conversion efficiency described in the first embodiment and the above-described adjustment of the linear attenuation coefficient are alternately repeated, thereby obtaining an appropriately corrected phosphor conversion efficiency. For example, the first decomposition unit 121 performs material decomposition to the water image W and the fat image A using the phosphor conversion efficiency determined by the processing (FIG. 8) according to the first embodiment, and the ratio calculation unit 122 and the estimation unit 123 correct the linear attenuation coefficient using the result. A decomposition unit 113 shown in FIG. 8 corrects the phosphor conversion efficiency again by energy subtraction processing using the corrected linear attenuation coefficient. By the above-described processing or by repeating the above-described processing, a more appropriately corrected phosphor conversion efficiency can be obtained.

FIG. 14 is a graph showing the result of repetitively performing correction of the phosphor conversion efficiency and adjustment of the linear attenuation coefficient. As shown in FIG. 14, when phosphor conversion efficiency correction and linear attenuation coefficient adjustment are repetitively performed, the difference of the bone thickness B by the combination of different tube voltages can be made small, and the bone thickness B by the combination of different tube voltages can be made close to the true value.

After the correction of the phosphor conversion efficiency and the adjustment of the linear attenuation coefficient as described above are ended, X-ray imaging of, for example, (a part of) a person as the object 301 is performed. The attenuation rate image H at high energy and the attenuation rate image L at low energy obtained by capturing the person are supplied to the first decomposition unit 121 and the second decomposition unit 124, and the linear attenuation coefficient of the soft tissue is adjusted by the first decomposition unit 121, the ratio calculation unit 122, and the estimation unit 123. Using the phosphor conversion efficiency determined in advance using PMMA and the adjusted linear attenuation coefficient from the estimation unit 123, the second decomposition unit 124 calculates a material decomposition image (B/S) from the attenuation rate image H at high energy and the attenuation rate image L at low energy obtained by X-ray imaging of the person. As described above, when the adjusted linear attenuation coefficient and the corrected phosphor conversion efficiency are used in energy subtraction processing, the decomposition accuracy improves. Particularly, according to the second embodiment, the phosphor conversion efficiency and the linear attenuation coefficient can effectively be corrected by combining correction of the phosphor conversion efficiency by the correction method (first embodiment) with little influence of the linear attenuation coefficient and correction of the linear attenuation coefficient.

Note that in the first and second embodiments, the X-ray imaging apparatus 104 is an indirect type X-ray sensor using a phosphor. However, the disclosed technique is not limited to this form. For example, a direct type X-ray sensor using a direct conversion material such as CdTe may be used. In this case, for example, the efficiency when converting X-rays incident on the X-ray sensor into a pixel value can be used as the predetermined parameter that is the correction target. More specifically, as described in the first embodiment, the efficiency when converting X-rays into a pixel value is determined such that the dispersion of the result of energy subtraction processing obtained from a plurality of sets of X-ray images is reduced.

Also, in the first and second embodiments, a plurality of X-ray images by a plurality of X-ray energies are obtained by changing the tube voltage of the X-ray generation apparatus 101. However, the disclosed technique is not limited to this form. For example, the energy of X-rays radiated to the X-ray imaging apparatus 104 may be changed by temporally switching the filter of the X-ray generation apparatus 101. Also, the plurality of X-ray images need not always be X-ray images individually captured by irradiation of X-rays of different X-ray energies, and need only be X-ray images corresponding to a plurality of X-ray energies. For example, X-ray images corresponding to different X-ray energies may be obtained using the change of the X-ray energy in X-ray irradiation of one shot. More specifically, there is known a configuration in which the time of X-ray irradiation of one shot is time-divided, and a plurality of X-ray images corresponding to different X-ray energies are obtained based on image information obtained in each period. In the technique according to the present disclosure, an X-ray image obtained by this configuration can also be used. In the first and second embodiments, two X-ray energies are used as the target of energy subtraction processing. However, the disclosed technique is not limited to this form. Three or more X-ray energies may be used, and three or more thicknesses may be calculated. In the first and second embodiments, the X-ray energy is changed, thereby obtained an image of a different energy. However, the disclosed technique is not limited to this form. A plurality of phosphors 105 and a plurality of two-dimensional detectors 106 may be overlaid, and images of different energies may be obtained from the two-dimensional detector on the front side and the two-dimensional detector on the rear side with respect to the direction of incidence of X-rays. In the first and second embodiments, a case where a medical FPD is used has been described. However, the disclosed technique is not limited to this form, and for example, an industrial FPD may be used.

Also, in the first and second embodiments, energy subtraction processing is performed using the control computer 103 of the radiation imaging system. However, the disclosed technique is not limited to this form. For example, an image obtained by the control computer 103 may be transferred to another computer, and energy subtraction processing may be performed. For example, a configuration in which an obtained image is transferred to another personal computer via a medical PACS, and displayed after energy subtraction processing is performed is suitably used.

Also, in the first and second embodiments, a phosphor conversion efficiency is shown using the result of energy subtraction processing obtained for a plurality of sets each formed from a combination of images of a plurality of X-ray energies. However, the correction target is not limited to this. For example, as described above, if a direct type X-ray sensor is used, the efficiency when converting X-rays incident on the X-ray sensor into a pixel value can be the correction target. Furthermore, for example, a parameter associated with the characteristic of the two-dimensional detector 106 other than the phosphor conversion efficiency, such as the thickness of the phosphor 105 or the dose dependence (linearity) of the pixel 20 can be used as the correction target. For example, the thickness of the phosphor can be corrected by searching for the thickness $d_C$ of the phosphor, with which the dispersion ($\sigma$ in equation (4)) of the results (for example, the bone thicknesses B) of energy subtraction processing obtained using a plurality of sets is minimized while changing the thickness $d_C$ in equation (2). The linearity (dose dependence) of the pixel 20 can be corrected by, for example, optimizing a correction coefficient f(E) to be multiplied by the attenuation rate $I/I_0$ in equations (3). For example, a model of the correction coefficient f(E) is assumed, and the correction coefficient f(E) is determined such that the dispersion (for example, $\sigma$ in equation (4)) of the plurality of results of energy subtraction processing obtained using a plurality of sets is minimized.

Also, the predetermined parameter that is the correction target by the method according to the first embodiment is not limited to a parameter associated with the characteristic of the two-dimensional detector 106. For example, parameters corresponding to the conditions in imaging such as a radiation spectrum, the linear attenuation coefficient of the object, and scattered rays can also be the correction target. For example, the spectrum of X-ray energy can be corrected by determining a model of the spectrum such that the dispersion of the results of energy subtraction processing obtained using a plurality of sets each formed from a combination of different X-ray energies is minimized. Note that as the result of energy subtraction processing, the "bone thickness" as described in the first embodiment can be used. However, for example, the thickness of the object 301 (PMMA) and the effective atomic number can also be used. In this case, the model of the spectrum is determined such that the dispersion of the results of each of the two values, the "thickness" and the "effective atomic number", becomes minimum (or close to the minimum).

Also, as described in the first embodiment, the error of the linear attenuation coefficient does not largely affect the dispersion of the results of energy subtraction processing obtained using a plurality of sets each formed from a combination of images of different X-ray energies. Hence, the effect of correcting the linear attenuation coefficient by the method of the first embodiment is not large. In principle, however, the "linear attenuation coefficient" can be the correction target. When correcting the linear attenuation coefficient, the characteristic of the change of the attenuation coefficient to the X-ray energy is approximated by a predetermined model (for example, a high order function model), and the model of the linear attenuation coefficient is determined such that the dispersion of the results of energy subtraction processing is reduced. Alternatively, when correcting the linear attenuation coefficient of a specific material, the ratio of a plurality of materials that form the specific material may be optimized such that the dispersion of the plurality of results of energy subtraction processing obtained for the plurality of sets is reduced. For example, the linear attenuation coefficient of a soft tissue can be adjusted as shown by equation (6) using the ratio $\alpha$ of water and fat, as described in the second embodiment. Hence, the ratio $\alpha$ may be optimized such that the dispersion of the results of energy subtraction processing is reduced.

Furthermore, a correction coefficient used for scattered ray correction can be corrected using the method of the first embodiment. For example, one of the parameters of scattered ray correction is an OID (the distance between an object and a sensor). When the relationship between the OID and the scattered ray correction coefficient is adjusted such that the dispersion of the results of energy subtraction processing obtained using a plurality of sets each formed from a combination of X-ray energies is reduced, the correction coefficient of scattered ray correction can be optimized.

As described above, according to the present disclosure, the accuracy of energy subtraction processing can be improved.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-083993, filed May 23, 2022, which is hereby incorporated by reference herein in its entirety.

What is claimed is:

1. An information processing apparatus comprising:
at least one processor; and
at least one memory storing instructions, which when executed by the processor, cause the information processing apparatus to:
obtain a plurality of results by performing energy subtraction processing for each of a plurality of sets which are sets each formed from a plurality of radiation images corresponding to different radiation energies and in which combinations of radiation energies are different; and
determine a value of a predetermined parameter used in the energy subtraction processing such that a dispersion between the plurality of results is reduced.

2. The apparatus according to claim 1, wherein the instructions, when executed by the processor, further cause the information processing apparatus to:
obtain at least three radiation images corresponding to at least three radiation energies different from each other,
wherein each of the plurality of sets is formed from a plurality of radiation images selected from the at least three radiation images.

3. The apparatus according to claim 1, wherein the instructions, when executed by the processor, further cause the information processing apparatus to:
determine the predetermined parameter such that one of a standard deviation and a variance of the plurality of results obtained from the plurality of sets becomes small.

4. The apparatus according to claim 1, wherein the instructions, when executed by the processor, further cause the information processing apparatus to:

determine a model for approximating the predetermined parameter such that a dispersion of the plurality of results obtained from the plurality of sets becomes small.

5. The apparatus according to claim 1, wherein the instructions, when executed by the processor, further cause the information processing apparatus to:

determine the value of the predetermined parameter by determining a combination of values of a plurality of parameters used in a model representing the predetermined parameter such that a dispersion of the plurality of results is reduced.

6. The apparatus according to claim 5, wherein the model is one of a linear model and a high order function model.

7. The apparatus according to claim 5, wherein the instructions, when executed by the processor, further cause the information processing apparatus to:

determine a parameter of the model by grid search.

8. The apparatus according to claim 1, wherein the predetermined parameter is a phosphor conversion efficiency used in the energy subtraction processing.

9. The apparatus according to claim 1, wherein the instructions, when executed by the processor, further cause the information processing apparatus to:

obtain, as each of the plurality of results, a bone thickness obtained by the energy subtraction processing.

10. The apparatus according to claim 1, wherein the instructions, when executed by the processor, further cause the information processing apparatus to:

obtain the plurality of sets concerning each of a plurality of objects having different thicknesses and performs the energy subtraction processing, thereby obtaining the plurality of results for each thickness, and determine the value of the predetermined parameter such that a sum of a plurality of dispersions obtained by obtaining a dispersion of the plurality of results for each thickness is reduced.

11. The apparatus according to claim 1, wherein the instructions, when executed by the processor, further cause the information processing apparatus to:

correct a linear attenuation coefficient for one material of materials decomposed by the energy subtraction processing.

12. The apparatus according to claim 11, wherein the instructions, when executed by the processor, further cause the information processing apparatus to:

decompose into images of a plurality of materials that form the one material by performing material decomposition using the predetermined parameter, and correct the linear attenuation coefficient of the one material based on ratios of amounts of the plurality of decomposed materials.

13. The apparatus according to claim 11, wherein the instructions, when executed by the processor, further cause the information processing apparatus to:

determine the predetermined parameter again such that the dispersion of the plurality of results obtained by the energy subtraction processing using the corrected linear attenuation coefficient is reduced.

14. The apparatus according to claim 1, wherein the instructions, when executed by the processor, further cause the information processing apparatus to:

generate an image used for diagnosis by performing energy subtraction processing using the plurality of radiation images corresponding to the different radiation energies, which are the plurality of radiation images concerning an object of a diagnosis target, and the value of the predetermined parameter.

15. An information processing method comprising:

a step for obtaining a plurality of results by performing energy subtraction processing for each of a plurality of sets which are sets each formed from a plurality of radiation images corresponding to different radiation energies and in which combinations of radiation energies are different; and a step for determining a value of a predetermined parameter used in the energy subtraction processing such that a dispersion between the plurality of results is reduced.

16. A non-transitory computer-readable storage medium storing a program configured to cause a computer to execute an information processing method defined in claim 15.

17. A radiation imaging system comprising:

an information processing apparatus defined in claim 1; and an X-ray imaging apparatus including a two-dimensional detector.

\* \* \* \* \*